(12) United States Patent
Sangha

(10) Patent No.: US 9,052,254 B2
(45) Date of Patent: *Jun. 9, 2015

(54) EVIDENCE COLLECTOR WITH INTEGRAL QUANTIFIED REAGENTS AND METHOD OF MODULATING SPECIMEN DRYING TIME

(75) Inventor: Jangbir Sangha, Overland Park, KS (US)

(73) Assignee: The Bode Technology Group, Inc., Lorton, VA (US)

(*) Notice: Subject to any disclaimer, the term of this patent is extended or adjusted under 35 U.S.C. 154(b) by 837 days.

This patent is subject to a terminal disclaimer.

(21) Appl. No.: 13/034,541

(22) Filed: Feb. 24, 2011

(65) Prior Publication Data

US 2012/0220042 A1   Aug. 30, 2012

Related U.S. Application Data

(63) Continuation-in-part of application No. 12/714,477, filed on Feb. 27, 2010, now Pat. No. 8,696,595, and a continuation-in-part of application No. 11/653,116, filed on Jan. 12, 2007, now Pat. No. 8,075,850, and a (Continued)

(51) Int. Cl.
*G01N 1/28* (2006.01)
*G01N 33/50* (2006.01)
*B23P 11/00* (2006.01)
*G01N 1/02* (2006.01)

(52) U.S. Cl.
CPC ............ *G01N 1/02* (2013.01); *G01N 2001/022* (2013.01); *G01N 2001/027* (2013.01); *G01N 2001/028* (2013.01)

(58) Field of Classification Search
CPC .................. G01N 2001/022; G01N 2001/027; G01N 2001/028; G01N 2001/4027; G01N 1/4022; C12M 1/30; A61F 13/38
USPC ............... 436/177, 174; 435/30, 309.1, 309.2
See application file for complete search history.

(56) References Cited

U.S. PATENT DOCUMENTS

| | | | |
|---|---|---|---|
| 2,835,246 A | 5/1958 | Boettger |
| 3,346,135 A | 10/1967 | Haitsch |
| 3,674,007 A | 7/1972 | Freis |
| 3,976,195 A | 8/1976 | Cohen |

(Continued)

OTHER PUBLICATIONS

The Biological Evidence website, accessed by the examiner on Dec. 16, 2013 at <http://www.iape.org/emanual/biological_evidence.htm>, last updated on Apr. 25, 2007.*

(Continued)

*Primary Examiner* — Christopher A Hixson
(74) *Attorney, Agent, or Firm* — Polsinelli PC

(57) ABSTRACT

Apparatus and methods are provided for evidence specimen collection having integral reagent holders to hold reagent vials and having drying agent or desiccant holding areas that permit the renewal of the desiccant and permit the introduction of variously size desiccant qualities to allow modulation of the specimen drying time to achieve early stabilization of specimens while holding the specimen in an isolated drying area during storage and shipment and for simultaneous collection of multiple evidence samples with simultaneous storage, drying, marking, evidence security and shipping provided and with the provision for simultaneous storage, drying, marking, evidence security and shipping provided for a control specimen.

28 Claims, 10 Drawing Sheets

Related U.S. Application Data continuation-in-part of application No. 11/787,313, filed on Apr. 16, 2007, now Pat. No. 8,740,812, and a continuation-in-part of application No. 11/699,807, filed on Jan. 30, 2007, now abandoned.

(60) Provisional application No. 61/305,497, filed on Feb. 17, 2010, provisional application No. 61/172,771, filed on Apr. 26, 2009, provisional application No. 60/758,855, filed on Jan. 13, 2006, provisional application No. 60/792,057, filed on Apr. 14, 2006, provisional application No. 60/815,801, filed on Jun. 22, 2006.

(56) References Cited

U.S. PATENT DOCUMENTS

| | | | |
|---|---|---|---|
| 4,014,748 A | | 3/1977 | Spinner |
| 4,175,008 A | | 11/1979 | White |
| 4,211,323 A | | 7/1980 | Olsen |
| 4,223,093 A | * | 9/1980 | Newman et al. ............. 600/572 |
| 4,350,508 A | * | 9/1982 | Santoro et al. ............. 96/117.5 |
| 4,586,604 A | | 5/1986 | Alter |
| 4,620,548 A | | 11/1986 | Hasselbrack |
| D287,570 S | | 1/1987 | Olsen |
| D293,819 S | | 1/1988 | Alvi |
| 4,813,432 A | | 3/1989 | Saint-Amand |
| 4,873,193 A | | 10/1989 | Jensen |
| 4,917,867 A | | 4/1990 | Jensen |
| 5,078,968 A | | 1/1992 | Nason |
| D328,244 S | | 7/1992 | Hamilton et al. |
| 5,129,402 A | | 7/1992 | Koll et al. |
| 5,151,094 A | | 9/1992 | Hanifl |
| D355,119 S | | 2/1995 | Zimmermann et al. |
| 5,612,218 A | | 3/1997 | Busch et al. |
| D383,214 S | | 9/1997 | Brennan |
| D385,793 S | | 11/1997 | Marsal |
| 5,687,867 A | | 11/1997 | Lamoureux |
| D389,586 S | | 1/1998 | Brennan |
| D389,761 S | | 1/1998 | Thomas |
| 5,726,062 A | | 3/1998 | Numa et al. |
| 5,856,172 A | | 1/1999 | Greenwood |
| 5,921,972 A | | 7/1999 | Skow |
| D424,440 S | | 5/2000 | Wilkinson et al. |
| 6,187,269 B1 | | 2/2001 | Lancesseur |
| 6,200,275 B1 | | 3/2001 | Cesarczyk |
| D447,561 S | | 9/2001 | Rudzena et al. |
| 6,312,395 B1 | | 11/2001 | Tripp et al. |
| 6,350,415 B1 | | 2/2002 | Niermann et al. |
| D457,247 S | | 5/2002 | Iheme et al. |
| 7,201,525 B2 | * | 4/2007 | Mohiuddin .................. 401/134 |
| D555,802 S | | 11/2007 | Couling et al. |
| 7,429,805 B2 | | 9/2008 | Hamel et al. |
| 7,452,714 B2 | | 11/2008 | Eversdijk |
| D612,513 S | | 3/2010 | Hendricks et al. |
| 2002/0057991 A1 | | 5/2002 | Kelly |
| 2003/0101523 A1 | | 6/2003 | Lepley |
| 2003/0113906 A1 | | 6/2003 | Sangha et al. |
| 2004/0082878 A1 | | 4/2004 | Baldwin |
| 2004/0211744 A1 | | 10/2004 | Marzokah |
| 2005/0009200 A1 | | 1/2005 | Guo |
| 2005/0010132 A1 | | 1/2005 | Pestes et al. |
| 2005/0059906 A1 | | 3/2005 | Tsaur |
| 2005/0252820 A1 | | 11/2005 | Sanchez-Felix et al. |
| 2006/0175280 A1 | | 8/2006 | Anraku et al. |
| 2006/0192098 A1 | | 8/2006 | Danylewych-May |
| 2007/0255175 A1 | | 11/2007 | Sangha |
| 2007/0299364 A1 | * | 12/2007 | Sangha ......................... 600/572 |
| 2008/0206740 A1 | | 8/2008 | Skiffington |
| 2008/0254550 A1 | | 10/2008 | Nathaniel |
| 2009/0043226 A1 | | 2/2009 | Elwell |
| 2009/0215159 A1 | | 8/2009 | Kirby |

OTHER PUBLICATIONS

Pang and Cheung, "Double swab technique for collecting touched evidence", Legal Medicine, vol. 9, pp. 181-184, Feb. 22, 2007.
Bode SecurSwab(TM) Collectors, Product Note, www.bodetech.com, Aug. 2008.
Bode SecurSwab(TM) Duo-V System, www.bodetech.com, 2010.

* cited by examiner

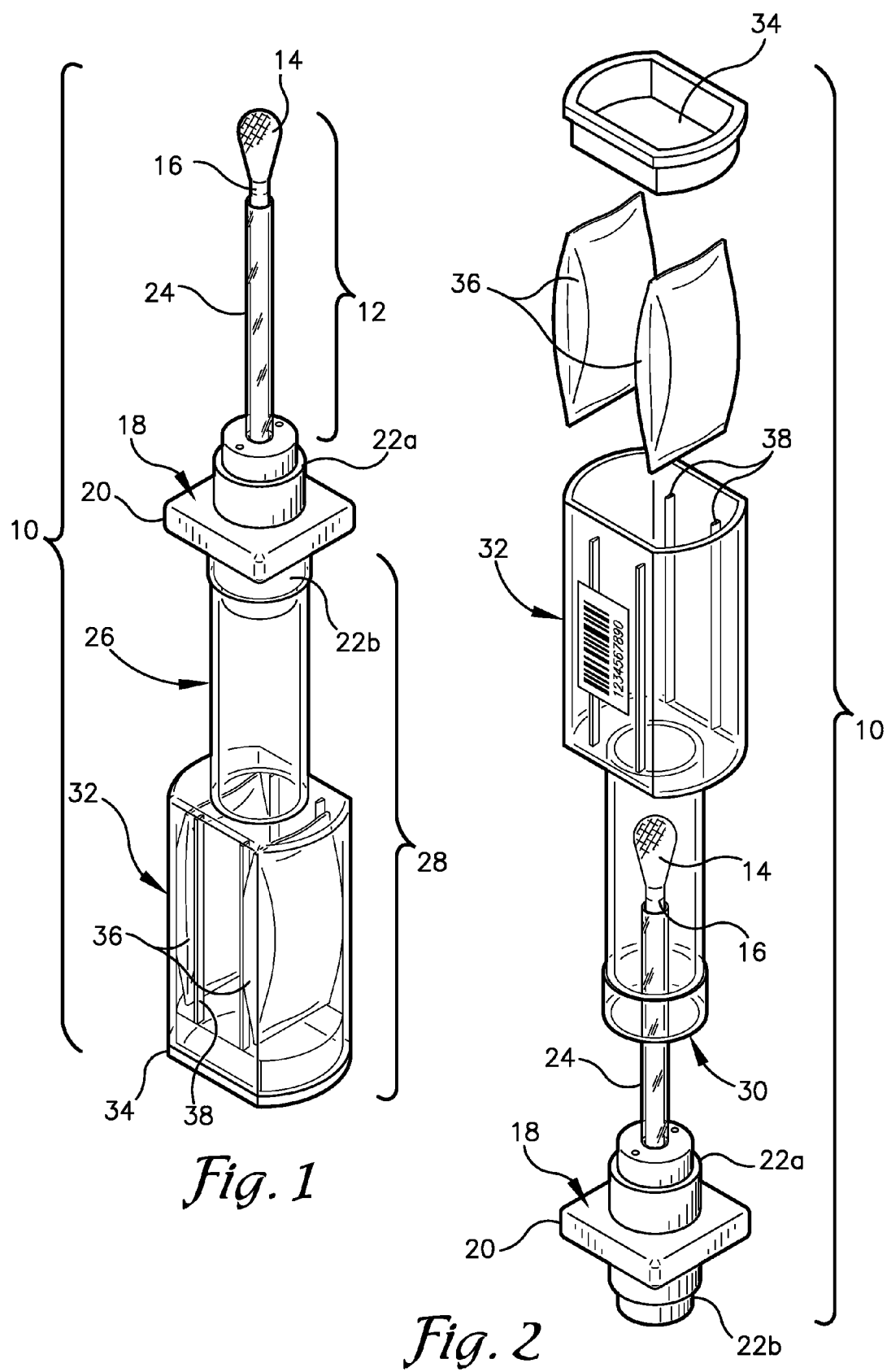

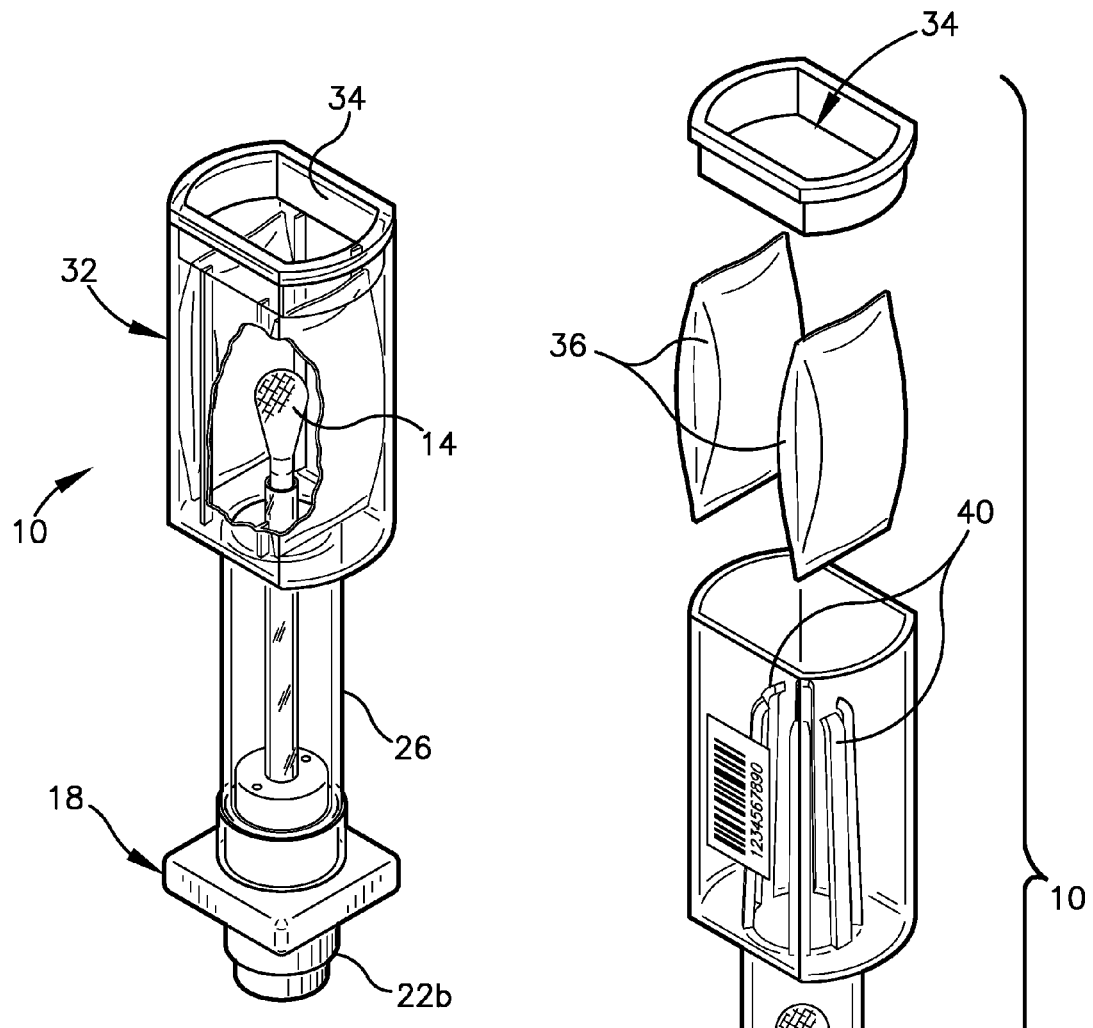

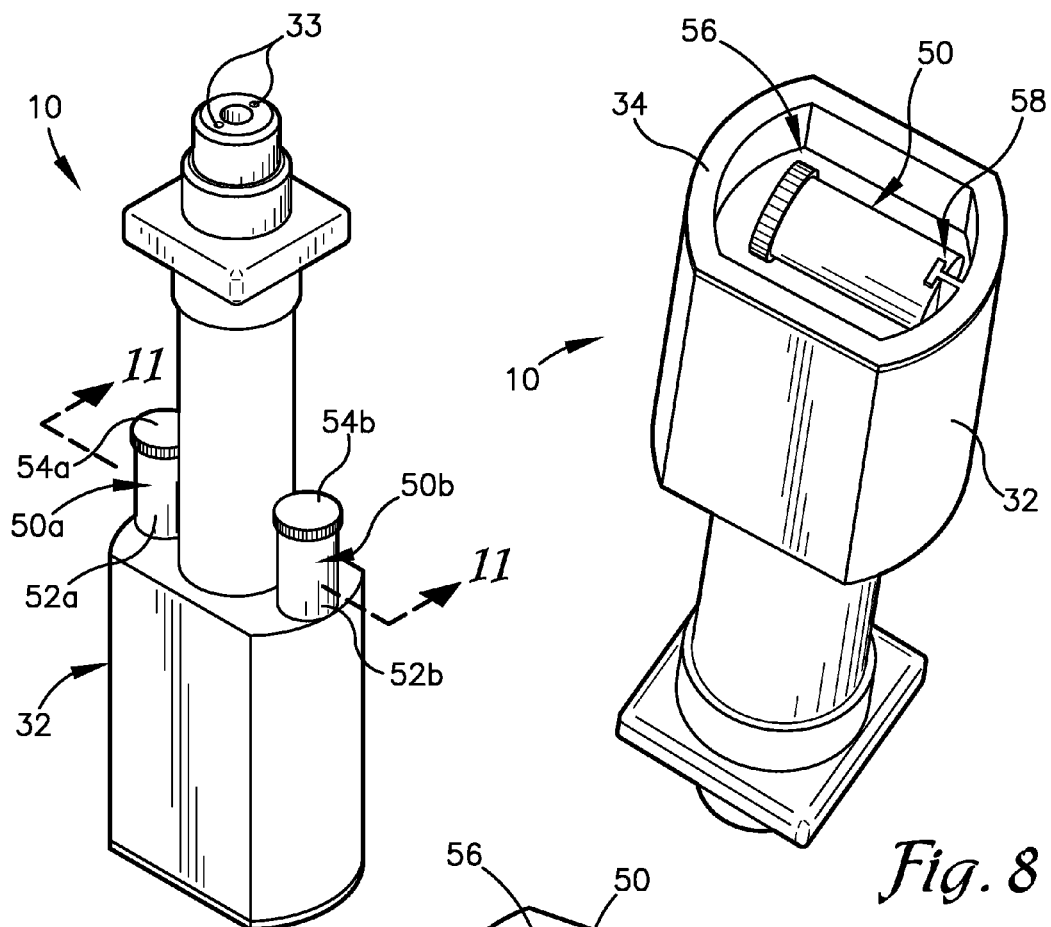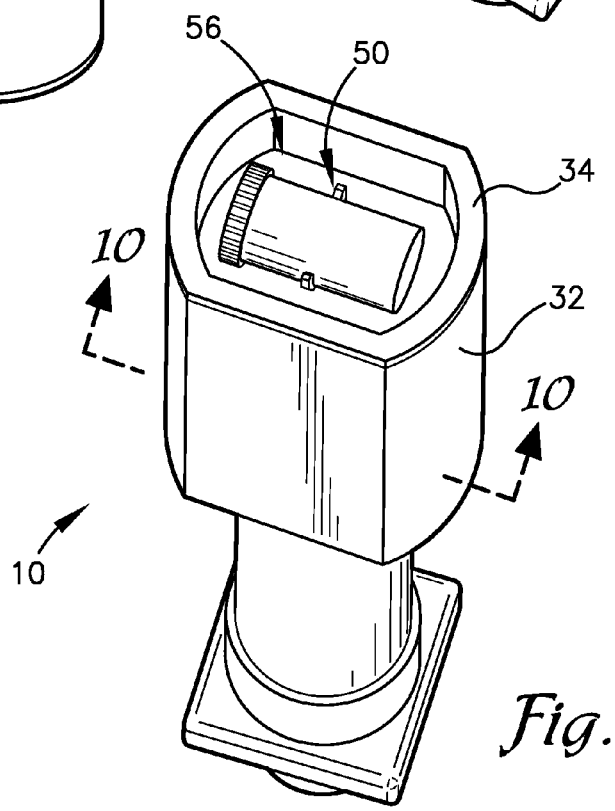

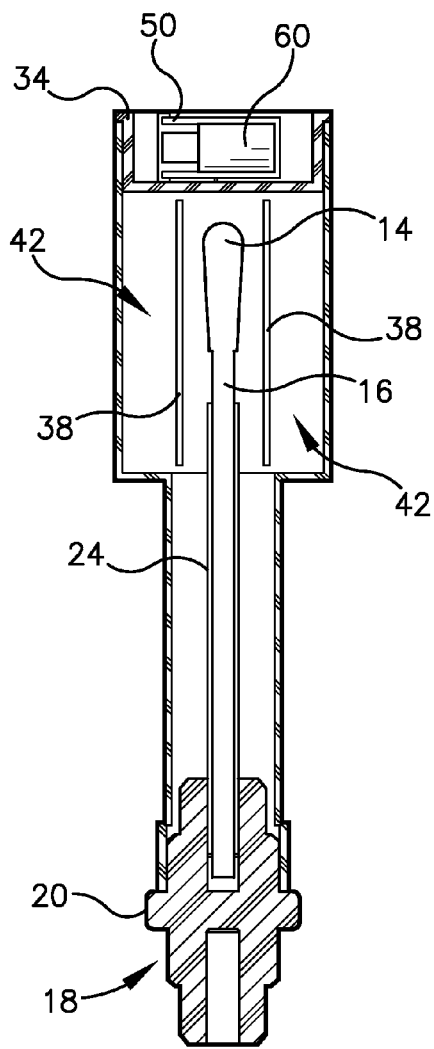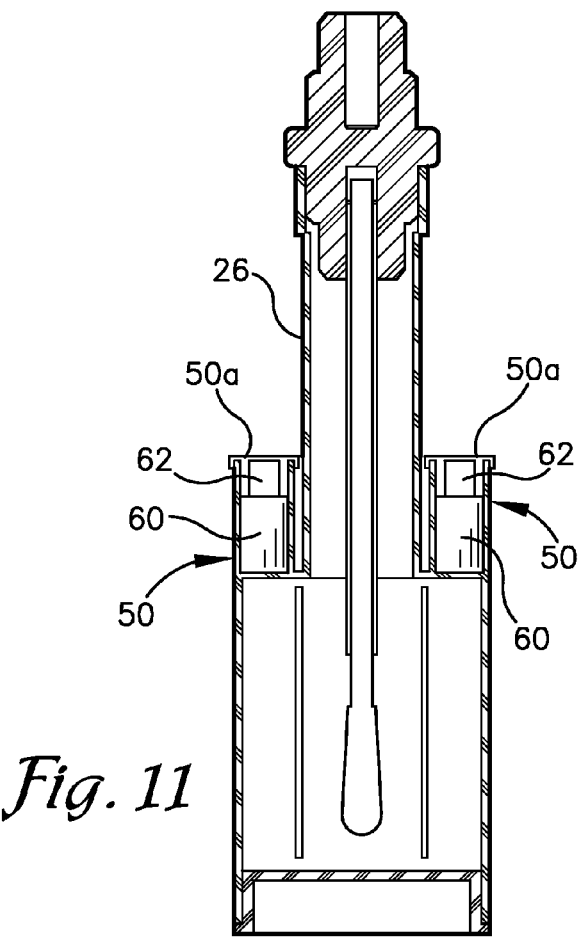
Fig. 10
Fig. 11
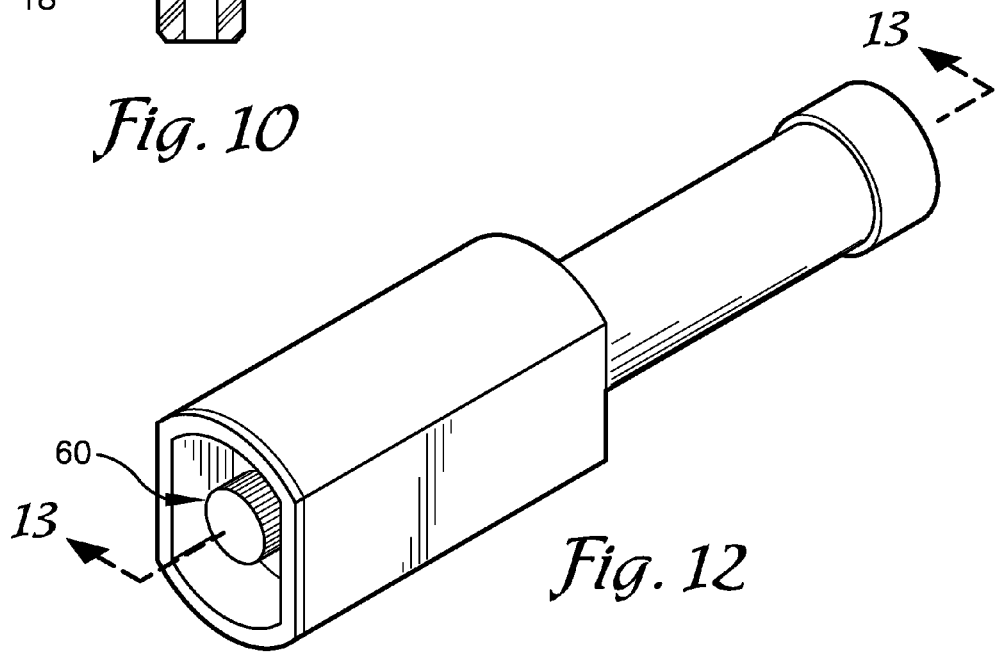
Fig. 12

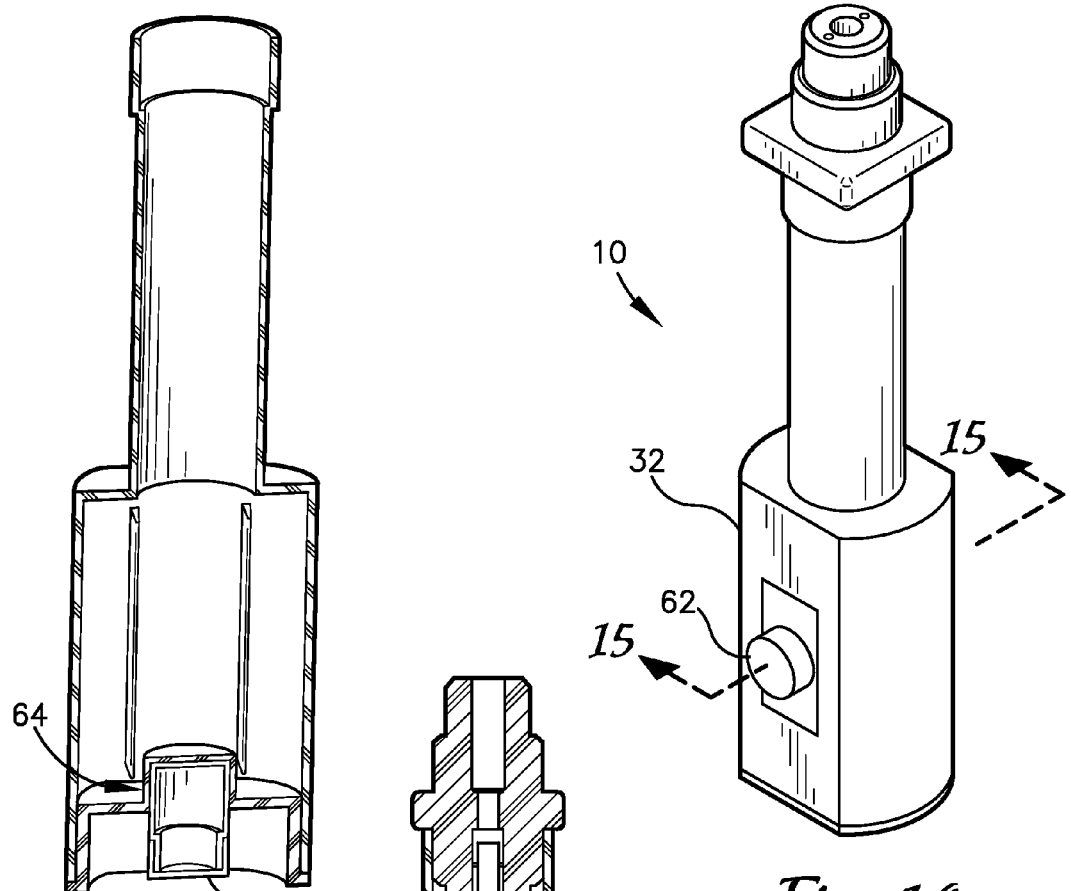
Fig. 13
Fig. 14
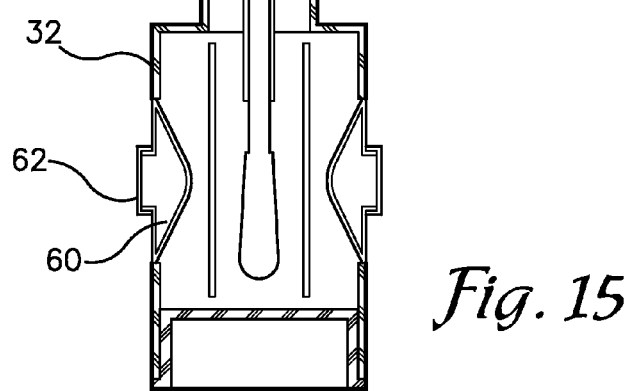
Fig. 15

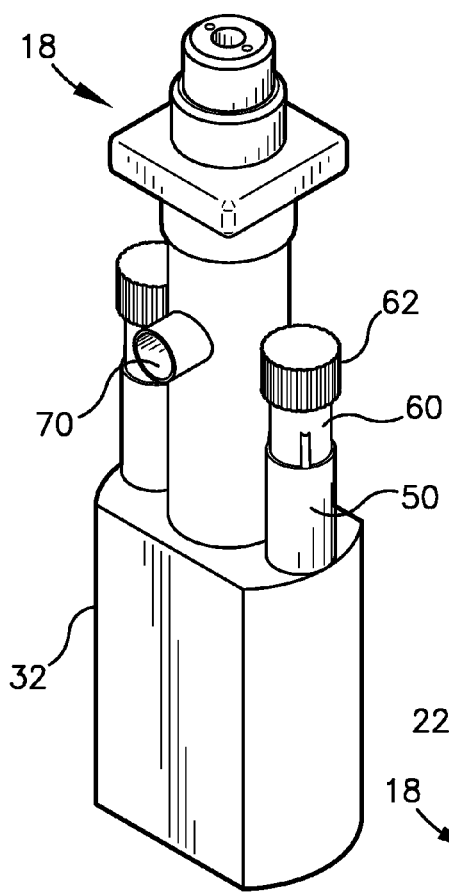
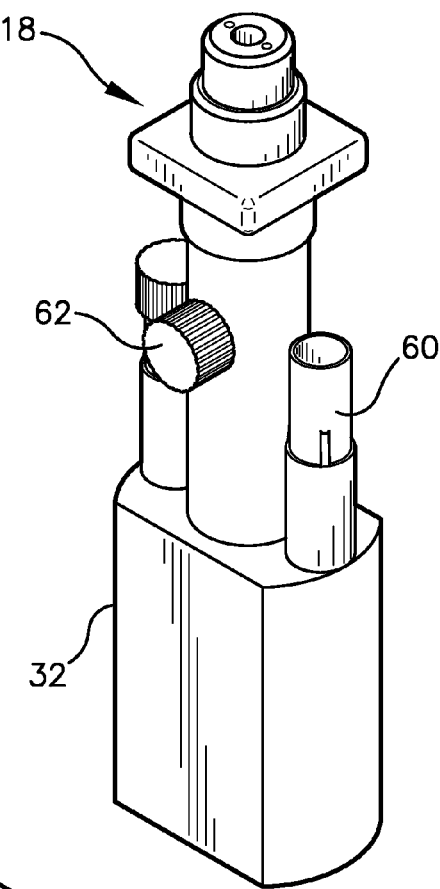
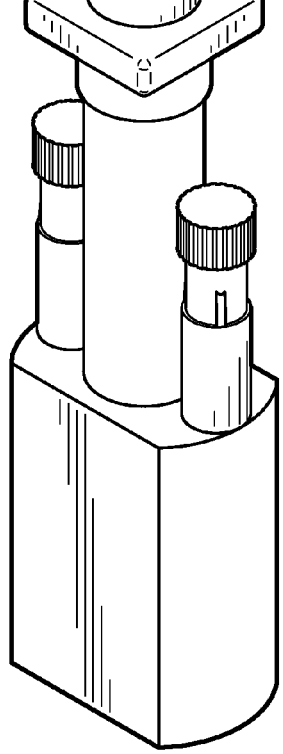
Fig. 16
Fig. 17
Fig. 18

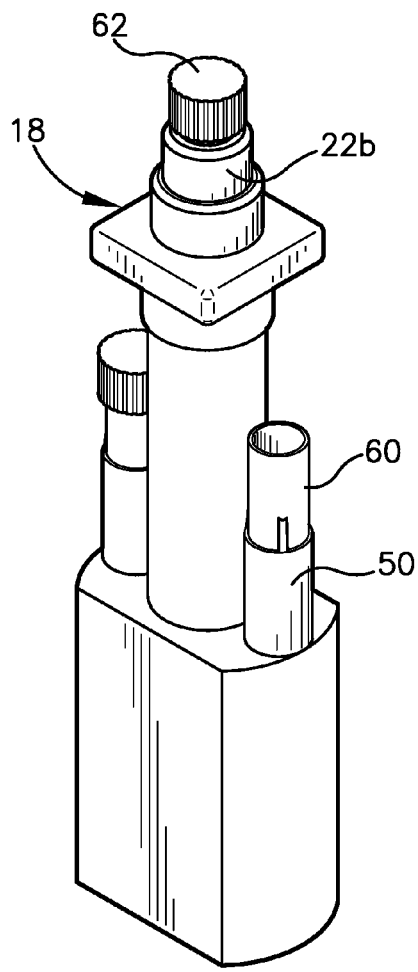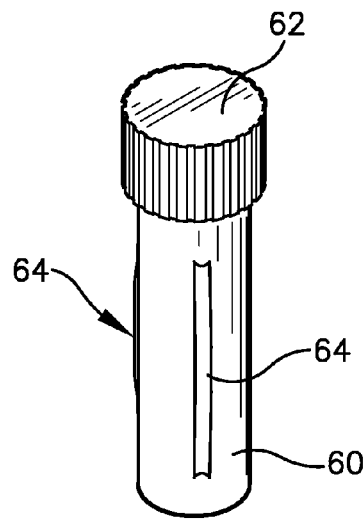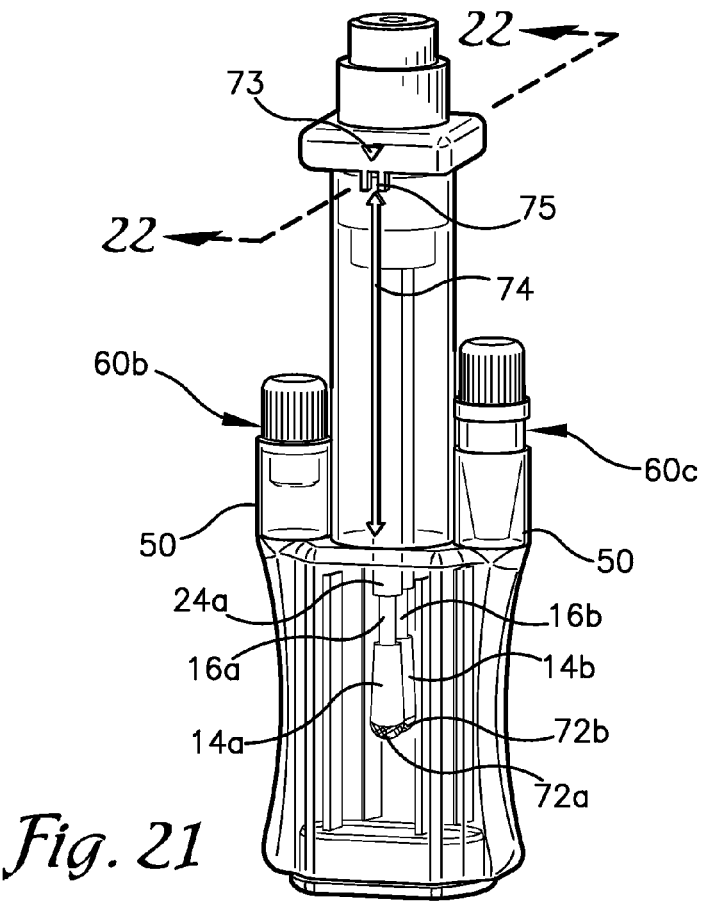
Fig. 19
Fig. 20
Fig. 21

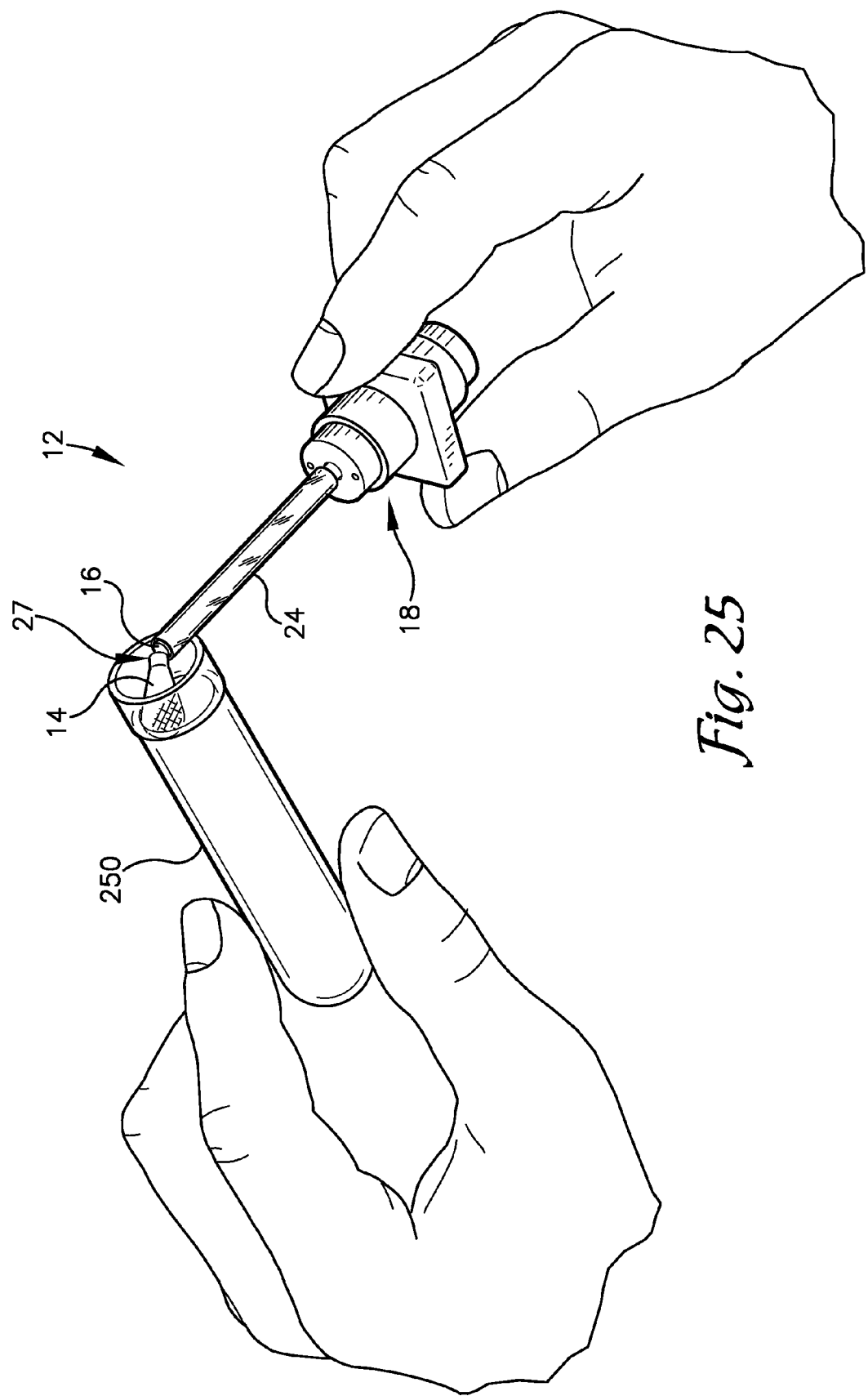

EVIDENCE COLLECTOR WITH INTEGRAL QUANTIFIED REAGENTS AND METHOD OF MODULATING SPECIMEN DRYING TIME

CROSS REFERENCE TO RELATED APPLICATION

This application claims priority under 35 U.S.C. 119(e) and under 35 U.S.C. 120 to U.S. application Ser. No. 12/714,477 filed Feb. 27, 2010 and U.S. Provisional Application No. 61/305,497 filed Feb. 17, 2010 and U.S. patent application Ser. No. 11/653,116 filed Jan. 12, 2007 based upon U.S. Provisional Application Ser. No. 60/758,855 filed Jan. 13, 2006 and U.S. application Ser. No. 11/787,313 filed Apr. 16, 2007 based upon U.S. Provisional Application 60/792,057 filed Apr. 14, 2006 and U.S. Provisional Application Ser. No. 61/172,771 filed Apr. 25, 2009, based upon copending U.S. application Ser. No. 11/699,807 filed Jan. 30, 2007 based upon U.S. Provisional Application 60/815,801 filed Jun. 22, 2006 all of which are incorporated herein by reference.

FIELD OF THE INVENTION

The field of the invention is directed to apparatus and methods for field collection and transport and analysis of laboratory specimens and crime scene evidence samples. The field of the invention also relates to a method of modulating the drying time of such specimens or evidence samples after collection to achieve rapid drying of the specimens or evidence samples based on the quantity of specimen and the quantity of moisture present in the specimens or evidence samples.

BACKGROUND OF THE INVENTION

The present embodiments provide a specimen collection and drying and transport and storage device that can be used for laboratory and forensic purposes to gather samples and/or specimens and to then dry the sample and/or specimen during transport and/or storage prior to testing of the sample or specimen. All this can be accomplished in the present embodiments while providing assurance that the chain of custody has been preserved and that the collected specimen or sample has not been switched during the changing of the drying agent employed to dry the specimen.

More particularly, the embodiments relate to a specimen collection apparatus for collecting such samples and stabilizing the specimens and preserving them from contamination prior to laboratory analysis. Therefore, an apparatus is provided in which the specimen collector is enclosed after collection of the sample thereon to protect the sample from contamination. The embodiments also allow exposure of the specimen or evidence sample to a drying agent to dry and stabilize the specimen to promote specimen integrity by providing rapid drying soon after specimen collection. Further, the embodiments allow the user to renew, or change-out, exhausted drying agent without disturbing the specimen. And, the embodiments allow the user to select and insert variously sized desiccant packets to modulate the drying time of the collected specimen or sample depending upon user desires for the particular specimen or sample.

In one embodiment simultaneous, identical, dual specimen or sample collection is provided which allows two identical specimens to be simultaneously collected in one motion by the user and to then simultaneously deliver the dual and identical specimens to a single housing to thereby assure that the specimen or evidence samples receive simultaneous and identical protection, drying conditions and transport conditions. Further, the embodiment allows one of the two identical and simultaneously collected specimens to remain untouched or unused and to be archived without removal of the specimen from the original housing into which it was inserted after collection. This may be accomplished while allowing the other of the two identical and simultaneously collected specimens to be removed from the housing or for a portion thereof removed for testing.

Crime scene evidence is collected to establish facts related to a crime or a suspected crime and for identification and/or elimination of suspects and may be presented at a trial for the determination of guilt or innocence of accused individuals. Often, the evidence includes objects, documents, fingerprints, photographs of the scene, and the like. Additionally, the evidence may include unknown substances or substances with a suspected identity, where the identity needs to be determined or confirmed. Such substances may be very small in quantity, may be dispersed over a comparatively large area, and may include materials such as: body fluids, hairs, flakes of skin such as skin cells, fibers, drugs, various chemicals, gunpowder residue, flammable materials, tobacco ashes, cosmetics, and the like. Such materials may be collected at a scene and subjected to chemical and/or DNA analysis for identification or for association with a particular individual.

Currently, for collecting specimen samples, investigators typically use fibrous swabs, such as swabs made of fibers of cotton, cellulose, rayon, polyester, polyester foam and other types of fibers. Such swabs not only absorb liquids and solids suspended in liquids but also trap dry substances such as particulate materials. Prior to use, the swabs are kept in closed sterile bags or containers to maintain sterility. After specimen collection the swabs and are placed into a similar bag or container to avoid contamination of the sample gathered during transportation. Once the swab is placed in a container after specimen collection, the container is usually marked with a time, the date, the identity of the investigator and other information to establish a chain of custody of the sample.

Conventional swabs are formed of a "stick" such as a shaft of wood, tubular plastic, or tubular or rolled paper with a pad of cotton or other fiber, sponge material, or other absorbent material attached to the end of the shaft, either mechanically or by an inert adhesive. A problem with conventional swabs is that there is a danger of contamination of the sample if it is necessary to put the swab down, for example, to open a bag or container in which the swab will be placed. Also, if it is necessary to set the swab down to dry, in a propped up condition or extending over the edge of a table, there is a risk of contamination of the sample.

The present embodiments provide an apparatus and method for collecting solid, fluid or particulate evidence specimens related to any type of situation in which evidence collection is required. Such evidence collection can be associated with crime scenes or can simply be the collection of a DNA sample from a human being in the course of a traffic stop or a paternity investigation. Suitable specimens for collection using the present devices are, in general, that evidence which is located on a surface or on a human being and which can be physically contacted by an evidence collection device to thereby obtain a sample of the evidence. Examples of such evidence specimens might be any type of biological fluid, either wet or dried, such as blood, urine or saliva, or any unknown substance which is visible or invisible and which can be located allowing for collection of a specimen of the evidence and capture of such a sample on a specimen collector of the type described hereinafter. As previously mentioned, it will be appreciated that such specimen collection devices are widely used in criminal investigations, but also are used increasingly in traffic stop situations or traffic arrest situations in which it is desirable to obtain a DNA sample from the suspect as part of a criminal records database requirement.

Therefore, for proper evidence collection that can be used in court to support a conviction, it is necessary that investigators have at their disposal a device and method of collection that dries the collected specimen shortly after collection to promote sample integrity by stabilizing the specimen by drying. It is additionally important that the apparatus promotes accuracy of specimen collection and reproducibility of specimen collection and protection of specimens from contamination while providing a device that enables a verifiable chain of custody while allowing continuous renewal of drying agents positioned adjacent to the specimen and while providing quantified specimen dilution during collection procedures and all without contributing to contamination of the crime scene by introducing extraneous material into the crime scene.

SUMMARY OF THE INVENTION

A first embodiment provides a specimen collector and container which may be used to collect a specimen with the container operating as a handle for the manipulation of the specimen collector and then subsequently the container may be used to receive the specimen collector therein for drying of the specimen within the container and for shipping of the specimen in a protected manner to an evidence room or to a laboratory and while a drying agent in the container, capable of being renewed without disturbing the specimen, speeds the drying of the collected specimen.

In another embodiment, the present device provides a specimen collector and container having all the above features and further providing the crime scene investigator with interchangeable, quantified specimen collection reagents and variable specimen collection reagents, which due to the device structure are fully and accurately absorbable by the specimen collection swab.

In another embodiment, the collection device provides for a swab on a specimen collector which swab can be conveniently detached from the specimen collector and specifically from the shaft connecting the swab to the specimen collector through use of a coaxially mounted tube which surrounds the shaft on which the swab is mounted. The coaxially mounted tube is provided with a terminal end which is located proximate to an area on the shaft where it is desired to have a point of breakage, or break-point location on the shaft, to separate the swab from the shaft to allow the swab to be separated from the specimen collector and to allow the swab to be deposited within a separate container. Another embodiment allow the swab to be pushed off the shaft by the use of he coaxially mounted tube. Yet another embodiment is provided with dual specimen collectors to allow simultaneous collection of identical specimens onto separate swabs. Yet another embodiment provides a reagent vial cap retaining stand or projection to provide a specific, reproducible storage location for placement of the vial cap to avoid introduction of the cap into the crime scene by an investigator removing the cap from a reagent vile and placing the cap on a surface that in or adjacent to the specimen to be collected and part of the crime scene.

DESCRIPTION OF THE DRAWINGS

FIG. 1 is a top, front and right side perspective view of an embodiment showing the swab removed from the holder and the swab reversed and inserted into the neck of the holder to allow the holder to act as a handle for the swab during specimen collection procedures and showing fixed desiccant retainers holding the desiccant packets at a set distance from the area occupied by the swab when it is inserted into the holder;

FIG. 2 is a bottom, back and left side exploded view of the embodiment of FIG. 1 showing the desiccant chamber cap spaced from the desiccant chamber and two desiccant packets removed from the desiccant chamber and showing within the desiccant chamber the fixed desiccant retainers or guards that hold the desiccant packets at a specific distance from the swab while allowing insertion of desiccant packets into desiccant chamber and showing the swab aligned for insertion into the holder for drying, transport and protection from contamination;

FIG. 3 is bottom, back and left side perspective view of an embodiment showing the swab inserted into the holder where is becomes positioned between the desiccant packets held in the desiccant chamber to permit drying of a specimen collected on the swab during storage and transportation of the swab within swab holder to a laboratory for analysis of the specimen;

FIG. 4 is a bottom, back and left side exploded view of an embodiment similar to that of FIG. 2, but showing the desiccant being retained by multiple flexible retainers or guards that accommodate desiccant packets of various sizes and allow variation in the distance between the swab and the desiccant packet thereby allowing for variation in the speed of specimen drying and allow for accommodation of specimens of greater volume which may require a larger amount of desiccant in the packets to achieve the desired degree of specimen dryness during transport of the collected specimen in the holder;

FIG. 7 is a top, front and right side perspective view of an embodiment similar to that shown in FIGS. 1-6 and having reagent holders mounted thereon;

FIG. 8 is a bottom rear and left side perspective view of a first variation of the device and showing a "T-shaped" securing structure on the bottom of the embodiment for holding a vial to the bottom of the embodiment;

FIG. 9 shows a bottom and front and left side prospective view of a second variation of the device and showing a friction-fit "C-shaped" securing structure for holding a vial to the bottom of the embodiment;

FIG. 10 is a cross-section view taken along line 10-10 of FIG. 9 and showing of the embodiment shown in FIG. 3 with the vial inside the exterior container held by the "C-shaped" securing structure and showing the solid construction of central section or central member 20 which may be drilled through if desired to provide gas communication through the closure;

FIG. 11 is a cross-section view taken along line 11-11 of FIG. 7 and showing reagent vials within the reagent holders and also showing the solid construction of central section or central member 20 which may be drilled through to provide gas communication through the closure;

FIG. 12 is a left side, front and bottom perspective view of another embodiment showing a reagent vial held in the bottom of the embodiment;

FIG. 13 is a cross-section view taken along line 13-13 of FIG. 12 and showing the insertion of the reagent vial into a cavity in the bottom of the device and held there by a frictional fit;

FIG. 14 is a front right side and top perspective view of an embodiment of the embodiment having a vial formed in the sides of the device and a cap thereon with the structure of the embodiment walls also forming the walls of the vial;

FIG. 15 is a cross-section view taken along line 15-15 of FIG. 14 and showing the formation of the vials on the front and back sidewalls of the embodiment and showing the solid construction of central section or central member 20 which may be drilled through to provide gas communication through the closure;

FIG. 16 is a front, right side and top perspective view of an alternate embodiment of the embodiment of FIG. 1 and having a vial and cap insert that can be placed into a securing sleeve on the embodiment and having a cap receptacle for holding the vial cap to avoid contamination of a crime scene through the introduction of external materials into the crime scene such as the cap that closes the vial of the present embodiment;

FIG. 17 is a front, right side and top perspective view of the embodiment of FIG. 22 and showing the cap removed from the vial and placed on the cap receptacle to hold the vial cap to avoid contamination of a crime scene through the introduction of external materials into the crime scene such as the cap that closes the vial of the present embodiment;

FIG. 18 is a front, right side and top perspective view of an alternate embodiment and showing the cap receptacle for holding the vial cap included as part of the cap that seals the body of the container;

FIG. 19 is a front, right side and top perspective view of the embodiment of FIG. 18 and showing the cap removed from the vial and placed on the cap receptacle that is positioned on the cap that seals the body of the container;

FIG. 20 is a front and top perspective view of the vial and cap insert that may be used with the embodiment of FIGS. 24 and 25 and other embodiments;

FIG. 21 shows an embodiment having dual swabs on dual shafts with each shaft having a break-off tube coaxially mounted on the shaft to allow for simultaneous, dual specimen collection by a user and showing the alignment indicator and closure rotation lock on the closure and on the holder that allows the user to properly align the dual swab collector on the holder to provide proper spacing of the swabs from the desiccant and showing dual vial carriers made integrally with the body of the device and showing a closure rotation indicator and locking structure on the neck of the embodiment;

FIG. 25 shows a swab being separated from the shaft by use of a break-off tube coaxially mounted on the swab shaft.

DETAILED DESCRIPTION

Figure 5:
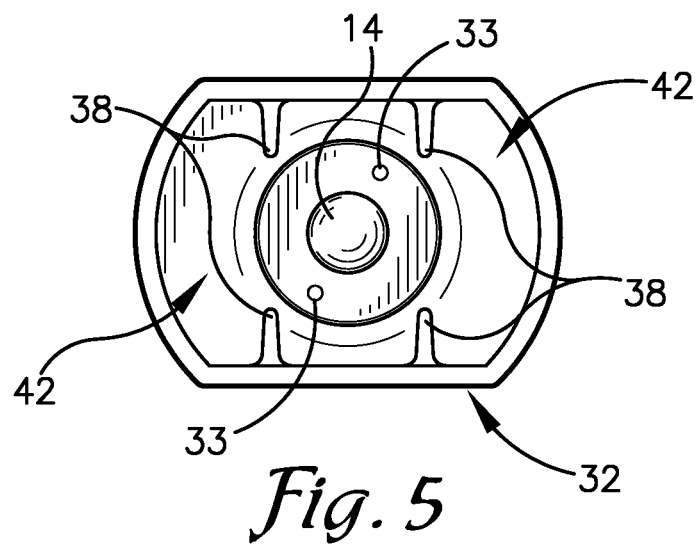
FIG. 5 is a bottom plan view of the desiccant chamber of the holder showing the swab positioned within fixed retainers or guards, the retainers or guards being spaced from the swab and any specimen on the swab to keep the specimen out of contact with the desiccant packets during drying and/or transport and/or storage.

As required, detailed embodiments of the present inventions are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

FIGS. 1-24 relate to embodiments of a unitized apparatus for collection and/or drying and/or transport and/or analysis apparatus 10 and a method for modulating drying time of the specimen through the use of user selectable and user sizeable desiccants and user renewable desiccants. Apparatus 10 comprises, generally, a swab mounted on a shaft, the shaft connected to a closure, and a housing or holder having a drying chamber containing a desiccant. The embodiments shown in FIGS. 1-6 are generally similar in construction but different in the means by which the desiccant is retained within the holder. The embodiments of FIGS. 7-19 include quantified reagent holders.

First referring to FIGS. 1-4 the unitized apparatus for collection and/or drying and/or transport and/or analysis apparatus 10 will be described. In FIG. 1 specimen collector 12 comprises a swab 14 mounted on a first end of a shaft 16 with the second end of the shaft connected to a closure 18. The closure 18 comprises a central member 20 having a stopper 22*a*, 22*b* extending from each of the two opposed sides of the central member. The specimen collector 12 further comprises a break-off tube 24 mounted coaxially on the shaft 16. The tube 24 is formed of a material that has greater rigidity than the material used to form shaft 16. A first end, of tube 24 is connected to closure 18 and a second end of tube 24 is configured to terminate at a selected location along shaft 16 at which it is desired to break shaft 16 to achieve separation of swab 14 and the portion of the shaft to which swab 14 is mounted from the remainder of shaft 16. This location on shaft 16 is referred to as the break-point location and will vary depending on the length of break-tube 24 that is mounted on shaft 16. Alternatively the break-tube 24 may be connected into closure 18 in a separable manner to allow tube 24 to be pulled from connection with closure 18 and pressed along or slid along shaft 16 until it contacts swab 14 whereupon it can be used to force swab 14 off of shaft 16 and into a container or other receptacle.

For clarity this type of separation of swab 14 from specimen collector 12 is shown in FIG. 25. In FIG. 25, it may be seen that swab 14 is pressed against a solid surface such as the side of container 250 and a bending motion is applied by the user to press swab 14 back toward tube 24 and closure 18. Upon sufficient pressure being applied, the shaft 16 will break at or near the terminus of tube 24. Then swab 14 and the portion of shaft 16 to which swab 14 is connected will separate from the portion of shaft 16 that is connected to closure 18. This allows the swab and the specimen that is collected onto the swab to be separated from the remainder of device 10 and separately placed into a reaction tube for analysis and/or an alternate container for shipment.

Again referring to FIG. 1 it will be appreciated that closure 18 comprising central member 20 and having a stopper 22a, 22b extending from each of the two opposed sides of the central member is shown with stopper 22a having shaft 16 and tube 24 connected thereto and with stopper 22b inserted into neck 26 of housing 28 of apparatus 10. FIG. 1 presents the embodiment in its open position. In the open position, specimen collector 12 has been removed from housing 28 and the closure 18 has been reversed and inserted into opening 30 (FIG. 2) of the neck 26 of housing 28 from which closure 18 and swab 14 on shaft 16 and break-off tube 24 were just removed. This reversal and insertion allows housing 28 to act as a handle for manipulating the swab 14 of specimen collector 12 during the collection of a specimen onto swab 14. The relatively large, flat surface of desiccant chamber 32 fits securely into the palm of the hand and provides a flat surface that will prevent rolling of the apparatus 10 if it is placed on a surface. When positioned on a surface the edge of closure 18 extends laterally beyond swab 14 and keeps swab 14 separated from any contact with adjacent contaminating surfaces. The closed position for apparatus 10 is shown in FIG. 3 wherein specimen collector 12 has been inserted into housing 28 and stopper 22a of closure 18 has been inserted into opening 30 (FIG. 2) of the neck 26 of housing 28 so that stopper 22a of closure 18 having swab 14 on shaft 16 and break-off tube 24 connected thereto all are inserted into housing 28.

Referring now to FIGS. 2 and 4 the housing 28 being further comprised of desiccant chamber 32 connected to neck 26 of housing 28, will be described. Desiccant chamber 32 is provided with resealable cover 34 that forms the bottom of housing 28. Cover 34 may be generally flat to allow apparatus 10 to stand on a surface. Cover 34 may be removably connected to desiccant chamber 32 or it may be permanently sealed to close chamber 32. It will be appreciated that the permanent sealing of chamber 32 by cover 34 may be accomplished at the time of manufacture or upon the insertion of a specimen on swab 14 into housing 28 or cover 34 may be used to permanently seal housing 28 at any time thereafter. Desiccant packets 36 of FIGS. 2 and 4 have been removed from desiccant chamber 32 to better show the fixed retainers 38 (FIG. 2) and flexible retainers 40 (FIG. 4) that hold desiccant packets 36 in position within desiccant chamber 32. It will be appreciated from the FIGS. 2 and 4 that fixed retainers extend from a sidewall of desiccant chamber 32 and flexible retainers are a plurality of flexible finger-like structures that extend downwardly from the top of desiccant chamber 32 and can accommodate desiccant packets of various sizes and shapes by flexing toward and away from the swab isolation area 41. When swab 14 is positioned within housing 28, as shown in FIG. 3, it may be seen that swab 14 situated between the retainers 38 (FIG. 2) or within retainers 40 (FIG. 4) in a swab isolation area 41 with the retainers 38, 40 holding desiccant packets 20 away from swab 14. It will be appreciated that swab 14 is positioned between, but not contacted by, desiccant packets 36 to avoid contamination of swab 14.

In FIG. 4 an embodiment similar to that of FIG. 2 is shown in an exploded view. In FIG. 4 desiccant chamber cover 34 is separated from the desiccant chamber 32 and the two desiccant packets 36 have been removed from the desiccant chamber 32. Visible within the desiccant chamber 32 are the flexible retainers 40 that allow variable spacing of the desiccant packets 36 from the swab 14. It will be appreciated that the flexible nature of flexible retainers 40 allows insertion of variously sized desiccant packets 36 into desiccant chamber 32. This is accomplished by the flexible retainers 40 being able to bend inwardly toward swab 14 to expand the distance between flexible retainers 40 and the walls comprising desiccant housing 32. Due to this repositionable nature of flexible retainers 40, user selectable quantities of desiccant and variable volumes of desiccant and variable sizes of desiccant packets can be introduced by the user into desiccant chamber 32 to change the drying time of a specimen captured on swab 14. Desiccant packets 36 are positioned to be in close proximity to swab 14 to absorb moisture from the specimen that is collected on swab 14. As the proximity of desiccant to moisture has a direct correlation to the rapidity of drying, it will be appreciated that the close, but spaced, proximity of the desiccant to swab 14 is particularly efficacious in speeding the drying of moisture that may be on swab 14. Such variation is made possible by flexible retainers 40. It also will be appreciated that resealable cover 34 permits the replacement of desiccant packets 36 at anytime during the use of device 10 and without the need to disturb swab 14 and/or any specimen thereon.

In FIG. 3 a perspective view is shown of the device 10 of FIGS. 2 and 4 with swab 14 inserted into housing 28. In this position swab 14 is positioned between desiccant packets 34 for drying and is protected within housing 28 for transport and/or storage. It may be observed that swab 14 is positioned between guards 38. In FIG. 3 a portion of the desiccant packets 36 have been removed and a portion of the wall of desiccant chamber 32 has been removed for clarity.

It will be understood that in FIG. 3, closure 18 has been reinserted into neck 26 to dispose swab 14 and shaft 16 and break-off tube 24 within housing 28. This positioning places swab 14 disposed between retainers 38, 40 and within desiccant chamber 32. It will be appreciated that flexible retainers 40 extend beyond the bottom of swab 14 to prevent objects inserted into desiccant chamber 32 from making inadvertent contact with swab 14. Those skilled in the art will appreciate that with desiccant chamber cover 34 removed, as shown in FIG. 4, that desiccant chamber 32 is open and accessible. It is in this configuration that desiccant packets 36 can be inserted, removed, renewed or increased or decreased in size by the user as may be indicated by the needs of the particular specimen on swab 14 or the need to speed up or slow down drying of the specimen on swab 14. It also may be observed in FIGS. 5 and 7 that closure 18 may be provided with air holes 33 that extend through closure 18. Air holes 33 can aid in the drying of the specimen and air holes 33 can be excluded from the embodiment completely if desired.

In FIG. 5 the fixed or rigid retainers 38 and the swab 14 are shown from a bottom view into desiccant chamber 32. In this view it may be seen that swab 14 is positioned between retainers 38 and spaced therefrom so as not to contact retainers 38 or the walls of desiccant chamber 32. Desiccant holding areas 42 extending between retainers 38 and the walls of desiccant chamber 32 are best observed in FIGS. 5 and 6. It will be appreciated that variously sized desiccant packets 36 can be inserted into desiccant holding areas 42 during drying and/or transport and/or storage. Once the desiccant packets 36 have become exhausted by absorption of moisture they may be replaced. This is accomplished by removing cover 34 withdrawing exhausted desiccant packets 36 and inserting new desiccant packets 36. Once replacement has been accomplished, the desiccant chamber resealable cover 34 may be replaced to again close desiccant chamber 32 to the outside.

Figure 6:
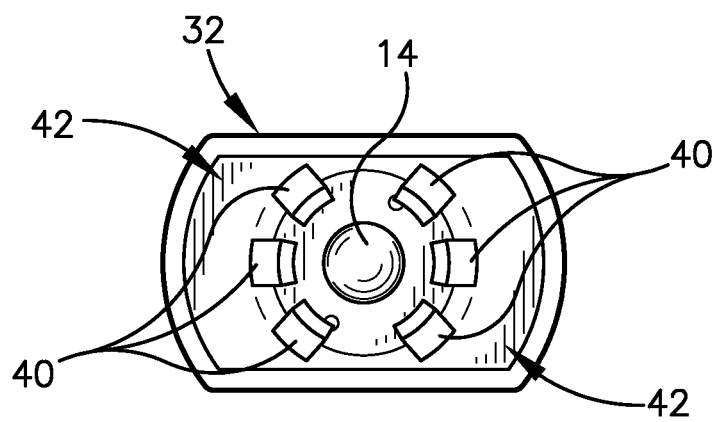
FIG. 6 is a bottom plan view of the desiccant chamber of the holder showing the swab positioned within a set of flexible retainers or guards the retainers being spaced from the swab, but being flexible at the point where the retainers contact the holder to permit the flexible retainers to accommodate variously sized desiccant packets to allow for variations in desired specimen drying time and variations in the specimen liquid content which can affect drying time as well as allowing for variation in the distance of the specimen from the desiccant which can change the drying time during storage and/or transport of the specimen.

In FIG. 6 the flexible guards 40 and the swab 14 are shown from a bottom view into desiccant chamber 32. In this view it may be seen that swab 14 is positioned within flexible guards 40 and spaced therefrom so as not to contact flexible guards 40 or the walls of desiccant chamber 32. It will be appreciated that the ends of flexible guard 40 bend inwardly to operate to deflect material, such as desiccant packets 36 when they enter desiccant chamber 32, from contacting swab 14 and any specimen thereon. Desiccant holding areas 42 extending between flexible guards 40 and the walls of desiccant chamber 32. It will be appreciated that as flexible guards 40 may be pushed away from desiccant chamber 32 walls that variously sized desiccant packets 36 can be inserted into desiccant holding areas 42 during drying and/or transport and/or storage. Once the desiccant packets 36 have been inserted, the desiccant chamber resealable cover 34 may be replaced to again close desiccant chamber 32 to the outside. It will be appreciated that the flexible guards 40 in particular allow the user to select and insert variously sized desiccant packets to modulate the drying time of the collected specimen or sample depending upon user desires for the particular specimen or sample. In addition the flexible guards 40 permit larger desiccant packet volumes to approach more closely to the swab 14 as it resides in the swab isolation area 41 since the flexible guards 40 can move inwardly toward the swab thereby placing the desiccant closer to the specimen. This configuration will modulate the drying of the specimen as the closer proximity of the desiccant to the moisture of the specimen on the swab will decrease the drying time of the specimen and enhance the stability of the collected specimen by drying the specimen faster.

Referring now to FIG. 7 an embodiment of a type shown in FIGS. 1-6 is shown further comprising the addition of reagent holders mounted on the top of desiccant chamber 32. Reagent holders 50a, 50b extend from desiccant chamber 32 and are molded in unitary fashion with desiccant chamber 32. The reagent holders 50a, 50b are comprised of a body 52a, 52b and a cap 54a, 54b. Caps 54a, 54b may be of the screw type or the friction fit type of cap.

Referring now to FIG. 8 and FIG. 9, embodiments are shown having the reagent holders 50 mounted on desiccant chamber removable cover 34. In the embodiment of FIG. 8, reagent holder 50 is held within an indention formed in cover 34. The indention being sufficient to allow the entirety of reagent holder 50 to sit within the indention while yet allowing apparatus 10 to stand on a flat surface with resalable cover 34. Such contact with the surface is shown in FIG. 7. In FIG. 8, reagent holder 50 is retained within indention 56 by a tongue and groove shaped arrangement with the groove being within the bottom of the reagent holder 50 and the tongue extending from removable cover 34 and being configured to be mateable with the groove in the bottom of the reagent holder 50. In FIG. 9, the reagent holder 50 is retained within indention 56 by C-shaped which provides a frictional fit capture of the reagent holder 50 within the C-shaped retaining clip.

Referring now to FIG. 10, a cross-section view taken along line 10-10 of FIG. 9 is shown. In FIG. 10, it can be seen that a device of similar construction to the device shown in FIGS. 1 and 2 is shown having desiccant holding areas 42 and retainers 38 and a swab 14 on shaft 16 having tube 24 coaxially mounted thereon. Also shown in FIG. 10 is reagent vial 60 which is in reagent holder 50. It will be appreciated by those skilled in the art that using a separate reagent vial 60 held within a reagent holder 50 that different reagent compositions and of different volumes may be rapidly and easily substituted into reagent holder 50 by simple substitution of a different reagent vial 60.

Referring now to FIG. 11, a cross-section view taken along line 11-11 of FIG. 7 is shown. In FIG. 11, reagent holders 50 are shown to either side of neck 26 with each vial 60 having a cap 62 thereon and reagent holder 50 having its own cap 50a serving to retain vial 60 within reagent holder 50.

Referring now to FIG. 12, an embodiment is shown having reagent vial 60 inserted into a depression formed in the surface of desiccant chamber receivable cover 34. In FIG. 13, a cross-section view taken along line 13-13 of FIG. 12 is shown. In FIG. 13, the cross-section view of the embodiment of FIG. 12 shows that cover 34 is provided with an indention 64 which is configured to capture vial 60 therein by a frictional fit between the bottom of vial 60 and the walls of indention 64.

In FIGS. 14 and 15, yet another embodiment of the reagent holder on the apparatus is shown. In FIG. 14, it can be seen that the reagent vial 60 is formed integrally with the sidewall of desiccant chamber 32. This may be more clearly seen in FIG. 15, which is a cross-section view taken along line 15-15 of FIG. 14. In FIG. 15, reagent vial 60 is shown as comprising an indention in the sidewall of desiccant chamber 32 and having cap 62 thereon to seal reagent vial 60.

Referring now to embodiments shown in FIGS. 16-20, embodiments having reagent holders and reagent vials are shown but also having the added advantage of having a cap stand included in the embodiment to retain a reagent holder cap or a reagent vial cap and to provide secure, reproducible placement in the keeping of the reagent or vial cap thereby to avoid loss of the vial cap and to avoid contamination of a crime scene in particular. The cap receptacle allows the evidence collection technician to avoid contamination of a crime scene by the inadvertent introduction of external materials into the crime scene. Specifically, the receptacle allows the cap that closes the vial to be placed in a specific, anticipated, repeatable location that is a part of the equipment brought to the scene by the evidence collection technician. In this manner the evidence collection technician will always know where to put the cap and where to locate it at the conclusion of the specimen collection. This provides a consistent and repeatable activity that can become a part of the evidence collection technicians method of practice and thereby reduce the introduction of external materials and potential extraneous DNA that might contaminate the crime scene.

Referring now to FIGS. 16 and 17, an embodiment is shown having a cap stand 70 extending from neck 26 of holder 28. In FIG. 17, it can be seen that a cap 62 has been removed from reagent vial 60 and has been placed onto cap holder 70 where cap 62 is retained during the course of a collection procedure performed with the embodiment shown in FIG. 17. It also will be appreciated that having the reagent holder 50 and reagent vial 60 positioned in upright fashion on the top of desiccant chamber 32 allows the investigator, particularly a crime scene investigator, to have the reagent contained in reagent vial 60 available for use in wetting the swab 14 which is attached to closure 18 without a need to attempt to manipulate additional devices and structures to wet the swab 14 or to find a suitable location to place holder 28 within the crime scene to free a hand to hold the reagent vial 60 while wetting swab 14 of a specimen collector 12 with a suitable reagent such as that which is contained in reagent vial 60 for a specimen collection.

Referring now to FIG. 18, an alternate embodiment is shown and which is similar to the embodiments of FIGS. 16 and 17 but in which the cap stand 70 is formed in the top of stopper 22b of closure 18. It will be appreciated that the embodiment of FIG. 18 operates in similar manner to the embodiment described in FIGS. 16 and 17. Such similar operation is shown in FIG. 19 wherein a cap 62 has been removed from a vial 60 and the cap 62 has been placed upon cap stand 70 which extends from stopper 22b closure 18. In FIG. 20, reagent vial 60 is shown of the type used in many of the embodiments described herein. Vial 60 is provided with longitudinal projections 64 which are compressible and which enhance the friction fit of reagent vial 60 within reagent holder 50 and which allow the passage of air in and about the sidewall of reagent vial 60 and the sidewall of reagent holder 50 when the two are insertably joined together as shown in FIG. 19. The importance of this feature will be appreciated by those skilled in the art who have contended with a moisture seal between two closely fitted surfaces and the barrier to separation of the two structures caused by the moisture seal preventing the intrusion of air and causing a need to overcome a vacuum which is created between the two surfaces when the withdrawal of the objects from insertion, one within the other, is attempted. Projection 64 assists in such separation while also providing secure frictional fit between vial 60 and reagent holder 50.

Figure 22:
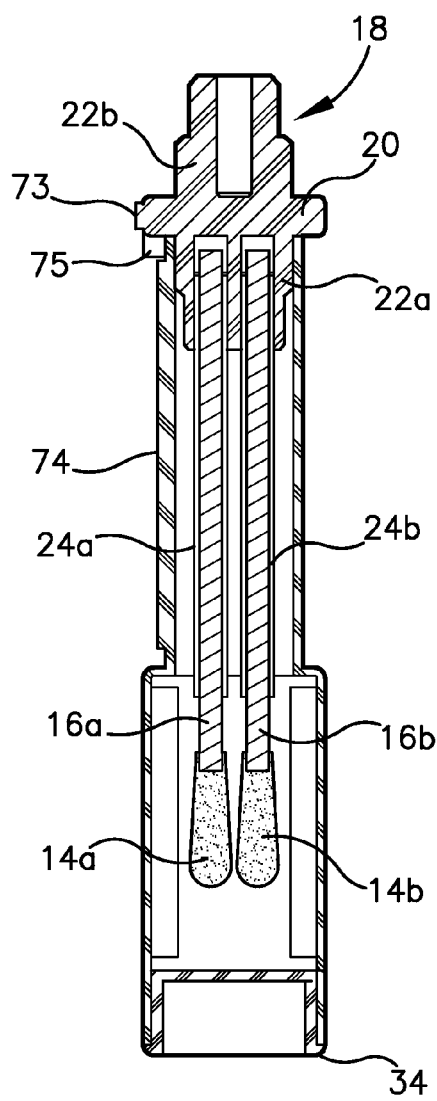
FIG. 22 shows a cross-section view of the embodiment of FIG. 21 taken along line 22-22 of FIG. 21 and showing the neck of the embodiment of FIG. 22 having the closure rotation indicator and locking structure 74 on the neck of the embodiment engaged with the closure rotation lock 75 on closure 18.

In FIGS. 21 and 22 an embodiment is shown having dual swabs 14a,b mounted on dual shafts 16a,b and having dual break-off tubes 24a,b coaxially mounted on each of the shafts. Both of these dual swab, shaft and break-off tube combinations are connected to the same stopper 22a extending from central member 20 of closure 18. The embodiment of FIGS. 21 and 22 allows the user to collect simultaneously, identical, dual specimens or samples 72a,b in one motion or in a single contact with a specimen or evidence location. Then the user can simultaneously deliver the dual and identical specimens 72a,b to a single housing 28 to thereby assure that the specimen or evidence samples receive simultaneous and identical protection and drying conditions and transport conditions are provided to the identical, dual specimens. The embodiment of FIGS. 21 and 22 permits a user to remove one of the two identical and simultaneously collected specimens 72a,b while allowing the other specimen or sample 72a,b to remain untouched or unused and to be archived without removal of the specimen from the original housing into which it was inserted after collection. This simultaneous, dual collection and protection of a specimen or evidence sample is of great importance for evidence collection as it allows collection of two identical specimens 72a,b under exactly the same conditions, from exactly the same location of the evidence, and permits the separate removal and testing of one of the dual identical specimens without any change or disturbance to the other specimen and while leaving one of the dual identical specimen fully intact and untouched for archiving and further or future testing. This can be highly important in providing a second identical specimen for test verification where an analysis method that is destructive of the specimen must be employed.

FIG. 21 an embodiment is shown having dual swabs 14a,b connected to dual shafts 16a,b and with each shaft having a break-off tube 24a,b coaxially mounted on the shaft. As previously described for FIG. 25, the break-off tubes 24a,b allow for the swab 14 to be separated from the shaft 16. It also will be appreciated that the embodiment of FIGS. 21, 22 is provided with desiccant packets 36 in desiccant chamber 32 to permit simultaneous, and identical drying conditions for the dual specimens. As previously described, when swabs 14a,b are positioned within housing 28, the swabs 14a,b are to be situated between the retainers 38 (FIG. 2) or within retainers 40 (FIG. 4) with the retainers 38, 40 holding desiccant packets 20 away from swab 14. It will be appreciated that it is important that swabs 14a,b be positioned between, but not contacted by, desiccant packets 36 to avoid contamination of swabs 14a,b. To assure the proper location of swabs 14a,b the embodiment of FIGS. 21, 22 is provided with alignment indicators on closure 18 and holder 28. In FIGS. 21 and 22 closure 18 is provided with indicator 73 on central member 20 and holder 28 is provided with indicator 74. In operation, a user upon inserting specimen collector 12 into holder 28 will observe the alignment of indicators 73 and 74 and then rotate closure 18 within holder 28 until the indicators 73, 74 are aligned one above the other as shown in FIG. 21. This alignment assures that the swabs 14a,b are positioned between retainers 38 or 40 in a position that provides uniform separation between each of swabs 14a,b and desiccant packets 20. In this manner the identical drying of swabs 14a,b is assured.

The embodiment of FIGS. 21 and 22 also includes a closure rotation lock 75 on the closure 18. During insertion of specimen collector 12 into holder 28 and after alignment of indicators 73, 74 the closure can be pressed downwardly into holder 28 to insert holder indicator 74 into closure rotation lock 75 to thereby prevent inadvertent rotation of specimen collector 12 within holder 28. In this manner the proper alignment of the dual swab collector on the holder to provide proper spacing of the swabs from the desiccant is assured during future use and transportation.

It will be appreciated that the embodiment of FIGS. 21 and 22 can be used to capture evidence at a crime scene that may be used as a control during analysis while providing exactitude in the identical handling of the control swab since both the control swab and the specimen swab are handled simultaneously during the collection and drying and transport phases of evidence collection and the evidence security will be identical for both specimens. In the case that one of the dual swabs may be a control the evidence collector would use a first of the two dual swabs to take a specimen of the area surrounding the evidence specimen of interest. Then the second swab would be used to obtain a sample of the evidence specimen as it existed in the crime scene. Then both swabs would be treated identically and simultaneously during the remainder of the collection and insertion into the housing and marking and evidence security and shipping procedures. If a specimen containing DNA was collected on the evidence swab, the control swab could be examined to determine if background DNA was present in the vicinity of the DNA evidence and if background DNA was present on the control swab the background DNA then could be removed from the analysis of the DNA found on the evidence swab.

Figure 23:
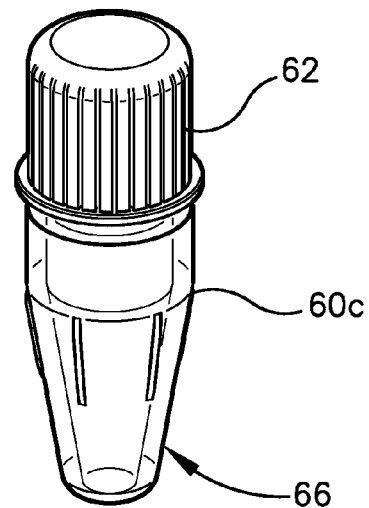
FIG. 23 is a front and top perspective view of a vial and cap insert that may be used with the embodiment shown in FIGS. 27 and 28 and other embodiments.

Also shown in FIG. 21, the provision for both a reagent holder 50 and a separate reagent vial 60 will be appreciated for allowing the use of variously sized reagent vials 60 which can contain precisely measured but different volumes of reagent to be applied to either swab 14 or to a specimen to be collected. As shown in FIG. 21, vial 60b is substantially smaller than is vial 60c. In providing individual vials for the provision of reagents to be applied to swab 14, the benefit is provided that exact quantization of the dilution of a specimen that is collected can be determined. In the prior art typical swab wetting procedure, an absorbent swab is held beneath a container nozzle and the technician attempts to apply individual drops of a reagent to the swab. The usual result is that the first drop or drops or substantial portions thereof bead up and fall off the swab due to the swab surface not being immediately absorbent. In the present embodiments, by providing an actual vial holding a reagent, the swab can be dipped into the vial where the pre-measured optimum quantity of a user selected reagent is held in contact with the swab 14 and complete absorption of the reagent onto the swab is accomplished. This absorption is further assisted by the pressure that can be brought to bear on the swab by the sidewalls of the vial 60 pressing against the swab 14 to assist in overcoming the surface tension present on the swab 14 thereby assisting in overall absorption of the reagent contained in vial 60. In FIG. 23, a vial of the type shown inserted in the reagent holder 50 of FIG. 21 is shown in greater detain and having inverted conical sidewalls 66 which further assists in the complete absorption of a small volume of reagent liquid on to swab 14. It will be appreciated that depending on what specimen is to be collected or what specimen is of interest to the investigator that the quantity and type of reagent in the vial may be user selected. For example if it is of particular interest the semen be immediately identified if it is present in the crime scene then the user or evidence technician can insert vials into the reagent holders that contain a semen reactive reagent to identify the presence of semen upon the swab contacting semen in the crime scene evidence. Or, if blood is of particular interest the evidence collection technician can insert vials into the reagent holders that contain a blood reactive reagent to identify the presence of blood upon the swab contacting the unknown crime scene specimen.

The quantified reagent vials 60 which are interchangeable within the reagent holders 50 are configured to provide a reproducible, quantitative wetting of the swab with a known amount of solution and which results in the wetting of the swab by a known volume this provides a quantified absorption of reagent onto the swab which is not possible with previous devices. As described above, the past procedures of attempting to add reagent in a drop-wise manner onto the swab could not produce a swab having a known quantity of reagent on the swab due to loss of drops or loss of portions of drops from the swab surface prior to absorption of the drop by the swab.

Figure 24:
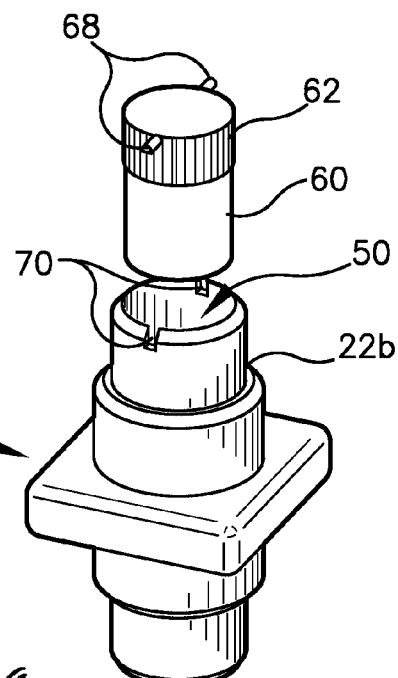
FIG. 24 shows an exploded perspective view of an embodiment of a closure which can be used with the embodiments described herein and having a reagent vial insertable into the closure for transport of a swab solution therein.

FIG. 24 shows a closure 18 having a reagent holder 50 formed into a stopper 22b for insertion of a vial 60 therein and with cap 62 of vial 60 being provided with flanges 68 which are captured within detents 70 of stopper 22b which assists in drawing vial 60 from stopper 22b as cap 62 will, when inserted into stopper 22b, be flush with the top of stopper 22b.

In FIG. 25 the method by which swab 14 is separated from shaft 16 by applying the terminal end of break-off tube 24 to a break-point 27 located on shaft 16. In FIG. 25 swab 14 is pressed against the side of container 250 and a bending motion is applied by the user to press swab 14 back toward tube 24 and closure 18. When sufficient pressure is applied shaft 16 will break at or near a break-point 27 which is adjacent the terminus of tube 24 as it is the terminus of tube 24 which establishes to point of application of bending force to shaft 14. When sufficient force is applied, shaft 16 will break and swab 14, and the portion of shaft 16 to which swab 14 is connected, will separate from the portion of shaft 16 that is connected to closure 18. This allows the swab and the specimen that is collected onto the swab to be separated from the remainder of device 10 for analysis and shipment. Alternatively, the break-off tube may be used as a swab pushed-off device. In this instance the break-off tube may be pushed by the user along the shaft to slide the break-off tube into contact with the swab. The break-off tube in this embodiment of configured to be a close, but slideable coaxial fit on the shaft and sufficiently smaller in diameter than the swab that the break-off tube will not slide over the exterior of the swab. In this embodiment the break-off tube will contact the swab and be used by the user to press the swab off the end of the shaft and into a reaction container or other tube or holder or shipping container.

I claim:

1. A method of specimen collection comprising the steps of:
    providing a specimen collector device comprising at least two specimen collectors extending from a first side of a container closure, each of the specimen collectors comprising:
        a specimen collection swab, the swab connected to a shaft having a first shaft end with the specimen collection swab thereon and a second shaft end connected to the container closure, the closure having first and second opposed sides of a central member, the specimen collector swabs being configured to simultaneously contact a specimen to collect a specimen sample on the swab, the specimen collector swabs being positioned to not contact the other specimen collector swab;
        a generally rigid tube mounted coaxially on the shaft, the tube having a first end connected to a first stopper structure and a second end terminating at a shaft break-point on said shaft said shaft-break point being positioned along said shaft at a location sufficiently spaced from said swab to permit the entire swab to be separated from the shaft when the shaft is broken at said shaft break-point;
        a housing for holding and drying and transporting the specimen collection swabs,
        the housing comprising:
            a desiccant chamber;
            a neck extending from the desiccant chamber the neck having an opening providing communication through the neck and into the desiccant chamber for passage of the swab from the neck and into the desiccant chamber;
            a swab isolation area in the desiccant chamber the swab isolation area aligned with the neck to receive the shaft mounted swab from the neck and to position the swab in the swab isolation area of the desiccant chamber;
            a desiccant holding area on at least one sidewall of the desiccant chamber of the swab isolation area, the desiccant holding area configured to retain a desiccant packet therein to absorb moisture from a specimen collected on the swab; and,
            an openable and closeable bottom on the desiccant chamber configured to permit removal of the desiccant packet from the desiccant holding area and insertion of the desiccant packet into the desiccant holding area while the swab is in the swab isolation area of the desiccant chamber;
    applying both swabs to a specimen;
    collecting a sample of the specimen onto both swabs;
    inserting both swabs into the neck of the housing to place the swabs in the swab isolation area of the desiccant chamber;
    aligning a first indicator located on the central member of the closure with a second indicator located on the holder, wherein both swabs are positioned within the desiccant holding area in a position that provides uniform separation between each of the swabs and the desiccant packets; and,
    drying both swabs within the desiccant chamber.

2. The method of claim 1 wherein the first swab is applied to the specimen and the second swab is simultaneously applied to an area adjacent the specimen but which does not include the specimen to simultaneously obtain a sample of the specimen and a sample of the area adjacent the specimen.

3. The method of claim 2 further comprising the steps of:
    analyzing the first swab sample of the specimen for data regarding the specimen to provide specimen data;

analyzing the second swab sample of the area immediately adjacent the specimen for data regarding the area, to provide area data, and using the area data as a control for comparison to the specimen data to interpret the specimen data.

4. The method of claim 1 wherein the steps of applying the swabs to a specimen and collecting a sample of the specimen onto both swabs are performed sequentially and not simultaneously.

5. The method of claim 1 further comprising the step of: applying a solution to one of said at least two swabs prior to the step of applying the swabs to a specimen.

6. The method of claim 1 further comprising the steps of: providing a flexible desiccant retainer to separate the desiccant holding area from the swab isolation area; inserting a desiccant packet into the desiccant holding area; and, permitting the flexible desiccant retainer to move toward or away from the swab isolation area to allow accommodation of the volume of the inserted flexible desiccant packet.

7. A method of specimen collection comprising the steps of:
providing a specimen collector device comprising at least two specimen collectors extending from a first side of a container closure, each of the specimen collectors comprising:
a specimen collection swab, the swab connected to a shaft having a first shaft end with the specimen collection swab thereon and a second shaft end connected to the container closure, the closure having first and second opposed sides of a central member, the specimen collector swabs being configured to simultaneously contact a specimen to collect a specimen sample on the swab, the specimen collector swabs being positioned to not contact the other specimen collector swab;
a housing for holding and drying and transporting the specimen collection swabs the housing comprising:
a desiccant chamber;
a neck extending from the desiccant chamber the neck having an opening providing communication through the neck and into the desiccant chamber;
a swab isolation area in the desiccant chamber the swab isolation area aligned with the neck to permit insertion of the shaft mounted swab through the neck and into the swab isolation area of the desiccant chamber the desiccant chamber having a desiccant holding area on at least one side of the swab isolation area the desiccant holding area configured to retain a desiccant packet therein to absorb moisture from a specimen collected on the swab; and,
an openable and closeable bottom on the desiccant chamber configured to permit removal of the desiccant packet from the desiccant holding area and insertion of the desiccant packet into the desiccant holding area while the swab is in the swab isolation area of the desiccant chamber;
applying both swabs to a specimen;
collecting a sample of the specimen onto both swabs;
inserting both swabs into the neck of the housing to place the swabs in the swab isolation area of the desiccant chamber;
aligning a first indicator located on the central member of the closure with a second indicator located on the holder, wherein both swabs are positioned within the desiccant holding area in a position that provides uniform separation between each of the swabs and the desiccant packets; and,
drying both swabs within the desiccant chamber.

8. The method of claim 7 wherein the first swab is applied to the specimen and the second swab is simultaneously applied to an area adjacent the specimen but which does not include the specimen to simultaneously obtain a sample of the specimen and a sample of the area adjacent the specimen.

9. The method of claim 8 further comprising the steps of:
analyzing the first swab sample of the specimen for data regarding the specimen to provide specimen data;
analyzing the second swab sample of the area immediately adjacent the specimen for data regarding the area, to provide area data; and,
using the area data as a control for comparison to the specimen data to interpret the specimen data.

10. The method of claim 7 further comprising the steps of:
providing a flexible desiccant retainer to separate the desiccant holding area from the swab isolation area;
inserting a desiccant packet into the desiccant holding area; and,
permitting the flexible desiccant retainer to move toward or away from the swab isolation area to allow accommodation of the volume of the inserted flexible desiccant packet.

11. The method of claim 7 wherein the steps of applying the swabs to a specimen and collecting a sample of the specimen onto both swabs are performed sequentially and not simultaneously.

12. The method of claim 7 further comprising the step of: applying a solution to one of said at least two swabs prior to the step of applying the swabs to a specimen.

13. A method of specimen collection comprising the steps of:
providing a specimen collector device comprising at least two specimen collectors extending from a first side of a container closure, each of the specimen collectors comprising:
a specimen collection swab, the swab connected to a shaft having a first shaft end with the specimen collection swab thereon and a second shaft end connected to the container closure, the closure having first and second opposed sides of a central member, the specimen collector swabs being configured to simultaneously contact a specimen to collect a specimen sample on the swab, the specimen collector swabs being positioned to not contact the other specimen collector swab;
a generally rigid tube mounted coaxially on the shaft, the tube having a first end connected to a first stopper structure and a second end terminating at a shaft break-point on said shaft said shaft-break point being positioned along said shaft at a location sufficiently spaced from said swab to permit the entire swab to be separated from the shaft when the shaft is broken at said shaft break-point;
a housing for holding and drying and transporting the specimen collection swabs the housing comprising:
a desiccant chamber;
a neck extending from the desiccant chamber the neck having an opening providing communication through the neck and into the desiccant chamber;
a swab isolation area in the desiccant chamber the swab isolation area aligned with the neck to permit insertion of the shaft mounted swab through the neck and into the swab isolation area of the desiccant chamber the desiccant chamber having a desiccant holding area on at least one side of the swab isolation area the desiccant holding area configured to retain a desiccant packet therein to absorb moisture from a specimen collected on the swab; and a bottom on the desiccant chamber;

applying both swabs to a specimen;

collecting a sample of the specimen onto both swabs;

inserting both swabs into the neck of the housing to place the swabs in the swab isolation area of the desiccant chamber;

aligning a first indicator located on the central member of the closure with a second indicator located on the holder, wherein both swabs are positioned within the desiccant holding area in a position that provides uniform separation between each of the swabs and the desiccant packets; and, drying both swabs within the desiccant chamber.

14. The method of claim 13 wherein the first swab is applied to the specimen and the second swab is simultaneously applied to an area adjacent the specimen but which does not include the specimen to simultaneously obtain a sample of the specimen and a sample of the area adjacent the specimen.

15. The method of claim 14 further comprising the steps of:
analyzing the first swab sample of the specimen for data regarding the specimen to provide specimen data;
analyzing the second swab sample of the area immediately adjacent the specimen for data regarding the area, to provide area data; and,
using the area data as a control for comparison to the specimen data to interpret the specimen data.

16. The method of claim 13 further comprising the steps of:
providing a flexible desiccant retainer to separate the desiccant holding area from the swab isolation area;
inserting a desiccant packet into the desiccant holding area; and,
permitting the flexible desiccant retainer to move toward or away from the swab isolation area to allow accommodation of the volume of the inserted flexible desiccant packet.

17. The method of claim 13 wherein the steps of applying the swabs to a specimen and collecting a sample of the specimen onto both swabs are performed sequentially and not simultaneously.

18. The method of claim 13 further comprising the step of:
applying a solution to one of said at least two swabs prior to the step of applying the swabs to a specimen.

19. A method of specimen collection comprising the steps of:
providing a specimen collector device comprising at least two specimen collectors extending from a first side of a container closure, each of the specimen collectors comprising:
a specimen collection swab, the swab connected to a shaft having a first shaft end with the specimen collection swab thereon and a second shaft end connected to the container closure, the closure having first and second opposed sides of a central member, the specimen collector swabs being configured to simultaneously contact a specimen to collect a specimen sample on the swab, the specimen collector swabs being positioned to not contact the other specimen collector swab;
a housing for holding and drying and transporting the specimen collection swabs the housing comprising a desiccant chamber;
a neck extending from the desiccant chamber the neck having an opening providing communication through the neck and into the desiccant chamber;
a swab isolation area in the desiccant chamber the swab isolation area aligned with the neck to permit insertion of the shaft mounted swab through the neck and into the swab isolation area of the desiccant chamber the desiccant chamber having a desiccant holding area on at least one side of the swab isolation area the desiccant holding area configured to retain a desiccant packet therein to absorb moisture from a specimen collected on the swab; and,
a bottom on the desiccant chamber;

applying both swabs to a specimen;

collecting a sample of the specimen onto both swabs;

inserting both swabs into the neck of the housing to place the swabs in the swab isolation area of the desiccant chamber;

aligning a first indicator located on the central member of the closure with a second indicator located on the holder, wherein both swabs are positioned within the desiccant holding area in a position that provides uniform separation between each of the swabs and the desiccant packets; and, drying both swabs within the desiccant chamber.

20. The method of claim 19 wherein the first swab is applied to the specimen and the second swab is simultaneously applied to an area adjacent the specimen but which does not include the specimen to simultaneously obtain a sample of the specimen and a sample of the area adjacent the specimen.

21. The method of claim 20 further comprising the steps of:
analyzing the first swab sample of the specimen for data regarding the specimen to provide specimen data;
analyzing the second swab sample of the area immediately adjacent the specimen for data regarding the area, to provide area data; and,
using the area data as a control for comparison to the specimen data to interpret the specimen data.

22. The method of claim 19 further comprising the steps of:
providing a flexible desiccant retainer to separate the desiccant holding area from the swab isolation area;
inserting a desiccant packet into the desiccant holding area; and,
permitting the flexible desiccant retainer to move toward or away from the swab isolation area to allow accommodation of the volume of the inserted flexible desiccant packet.

23. The method of claim 19 wherein the steps of applying the swabs to a specimen and collecting a sample of the specimen onto both swabs are performed sequentially and not simultaneously.

24. The method of claim 19 further comprising the step of:
applying a solution to one of said at least two swabs prior to the step of applying the swabs to a specimen.

25. The method of claim 1 wherein the steps of applying the swabs to a specimen and collecting a sample of the specimen onto both swabs are performed simultaneously and not sequentially.

26. The method of claim 7 wherein the steps of applying the swabs to a specimen and collecting a sample of the specimen onto both swabs are performed simultaneously and not sequentially.

27. The method of claim 13 wherein the steps of applying the swabs to a specimen and collecting a sample of the specimen onto both swabs are performed simultaneously and not sequentially.

28. The method of claim 19 wherein the steps of applying the swabs to a specimen and collecting a sample of the specimen onto both swabs are performed simultaneously and not sequentially.

* * * * *